United States Patent
Kimura

(10) Patent No.: US 9,776,004 B2
(45) Date of Patent: Oct. 3, 2017

(54) METHOD FOR TREATING PREMATURE EJACULATION AND METHOD FOR CONTROLLING PREMATURE EJACULATION TREATMENT DEVICE

(71) Applicant: ASTELLAS PHARMA INC., Tokyo (JP)

(72) Inventor: Yasuharu Kimura, Ibaraki (JP)

(73) Assignee: ASTELLAS PHARMA INC., Tokyo (JP)

(*) Notice: Subject to any disclaimer, the term of this patent is extended or adjusted under 35 U.S.C. 154(b) by 0 days.

(21) Appl. No.: 14/797,225

(22) Filed: Jul. 13, 2015

(65) Prior Publication Data
US 2017/0014632 A1    Jan. 19, 2017

(51) Int. Cl.
*A61N 1/36* (2006.01)
*A61N 1/05* (2006.01)

(52) U.S. Cl.
CPC ....... *A61N 1/36107* (2013.01); *A61N 1/0521* (2013.01); *A61N 1/36167* (2013.01)

(58) Field of Classification Search
CPC .................................................. A61N 1/36107
USPC .......................................................... 607/39
See application file for complete search history.

(56) References Cited

U.S. PATENT DOCUMENTS 8,135,478 B2    3/2012    Gross

2005/0096709 A1    5/2005    Skwarek et al.
2007/0255333 A1    11/2007    Giftakis et al.
2014/0303681 A1*  10/2014    Khan ................ A61N 1/36107
                                                        607/39

OTHER PUBLICATIONS

Uchio et al. "Cortical Evoked Responses from the Perineal Nerve". J Urol. 1999; 162:1983-1986. Rev Urol. 2000 Spring; 2(2): 98-99.*
Carlo Bettocchi, et al., "Ejaculatory disorders: pathophysiology and management", Nature Clinical Practice Urology, vol. 5, No. 2, Feb. 2008, pp. 93-103.
Stanley E. Althof, PhD, et al., "An Update of the International Society of Sexual Medicine's Guidelines for the Diagnosis and Treatment of Premature Ejaculation (PE)", Journal of Sexual Medicine, 2014, 11, pp. 1392-1422.
Ira D. Sharlip, MD, "Guidelines for the Diagnosis and Management of Premature Ejaculation", Journal of Sexual Medicine, 2006, 3(suppl. 4), pp. 309-317.
Selahittin Çayan, et al., "Advances in treating premature ejaculation", F1000 Prime Reports, 6:55, 2014, 6 pages.

(Continued)

*Primary Examiner* — Allen Porter, Jr.
(74) *Attorney, Agent, or Firm* — Oblon, McClelland, Maier & Neustadt, L.L.P.

(57) ABSTRACT

Methods of treating premature ejaculation include arranging one or more electrodes to face dorsal penile nerves (DPNs) of a patient with premature ejaculation, and applying an electro stimulation having a frequency and a current by which seminal fluid expulsion is not induced in the patient by the one or more electrodes during a time period from before the start of sexual intercourse to ejaculation. The electro stimulation reversibly extends an intravaginal ejaculatory latency time (IELT) of the patient. Methods of controlling a premature ejaculation treatment device are also provided.

4 Claims, 6 Drawing Sheets

(56) References Cited

OTHER PUBLICATIONS

Zhong Cheng Xin, et al., "Penile Sensitivity in Patients With Primary Premature Ejaculation", The Journal of Urology, vol. 156, Sep. 9, 1996, pp. 979-981.

Zhong Cheng Xin, et al., "Somatosensory Evoked Potentials in Patients With Primary Premature Ejaculation", The Journal of Urology, vol. 158, Aug. 1997, pp. 451-455.

G. C. Vignoli, M.D., "Premature Ejaculation: New Electrophysiologic Aproach", Urology, Jan. 1978, vol. XI, No. 1, 2 pages.

Zhang Hai-feng, et al., "Dorsal penile nerves and primary premature ejaculation", Chinese Medical Journal, 122, (24), 2009, pp. 3017-3019.

G.-X. Zhang, "Selective resection of dorsal nerves of penis for premature ejaculation", International Journal of Andrology 35, 2012, pp. 873-879.

J. David Prologo, et al., "Percutaneous CT-guided Cryoablation of the Dorsal Penile Nerve for Treatment of Symptomatic Premature Ejaculation", Clinical Study, Journal of Vascular and Interventional Radiology, 24, 2013 pp. 214-219.

Seref Basal, et al., "A Novel Treatment Modality in Patients With Premature Ejaculation Resistant to Conventional Methods: The Neuromodulation of Dorsal Penile Nerves by Pulsed Radiofrequency", Journal of Andrology, vol. 31, No. 2, Mar./Apr. 2010, pp. 126-130.

Robert Slappendel, et al., "The efficacy of radiofrequency lesioning of the cervical spinal dorsal root ganglion in a double blinded randomized study: no difference between 40° C. and 67° C. treatments", Pain, 73, 1997, pp. 159-163.

Edoardo S. Pescatori, et al., "Electrical Stimulation of the dorsal nerve of the penis evokes reflex tonic erections of the penile body and reflex ejaculatory responses in the spinal rat", The Journal of Urology, vol. 149, Mar. 1993, pp. 627-632.

Michael D. Staudt, MSc, et al., "Activation of Map Kinase in Lumbar Spinothalamic Cells Is Required for Ejaculation", Journal of Sexual Medicine, 2010, 7, pp. 2445-2457.

Natalie Kozyrev, MSc,, et al., "Activation of Gastrin-releasing Peptide Receptors in the Lumbosacral Spinal Cord is Required for Ejaculation in Male Rats", Original Research—Basic Science, Journal of Sexual Medicine, 2012, 9, pp. 1303-1318.

C.C. Yang, et al., "Reflex innervation of the bulbocavernosus muscle", BJU International, 2000, 85, pp. 857-863.

Jens Sønksen, et al., "Penile vibratory stimulation and electroejaculation in the treatment of ejaculatory dysfunction", International Journal of Andrology, 2002, 25, pp. 324-332.

Christian J. Nelson, et al., "Assessment of Penile Vibratory Stimulation as a Management Strategy in Men with Secondary Retarded Orgasm", Adult Urology, Urology, 69, (3), 2007, 4 pages.

Jeff A. Wieder, et al., "Anesthetic Block of the Dorsal Penile Nerve Inhibits Vibratory-Induced Ejaculation in Men With Spinal Cord Injuries", Adult Urology CME Article, Urology 55, (6), 2000, pp. 915-917.

Masayuki Tanahashi, et al., "Characterization of bulbospongiosus muscle reflexes activated by urethral distension in male rats", The American Journal of Physiology-Regulatory Integrative and Comparative Physiology, 303, 2012, pp. R737-R747.

L. Marson, et al., "Peripheral nerves mediating the urethrogenital reflex in urethaneanesthetized, acutely spinalized, male rats evoked by penile clamping or retraction", Neuroscience 2011, 391.09/VV45, 2011, Abstract, 2 pages.

V. Karicheti, et al., "Electrophysiological analyses of reflexes to bulbospongiosus (BS) and urethral rhabdosphincter (URS) muscles evoked by stimulation of pudendal afferent fibers reveals differences in adequate stimulus, patterns of activity, supraspinal control, and desensitization", Neuroscience 2011, 391.23/VV59, 2011, Abstract, 2 pages.

J. Zheng, et al., "Dorsal root (DR) compound action potential (CAP) evoked by electrical stimulation of sensory branch of pudendal nerve (ENS-SbPN)", Neuroscience 2012, 690.09/VV18, 2012, Abstract, 2 pages.

D. Jones, et al., "Electrical stimulation of the IMN evokes specific neuronal activation in the brain and spinal cord which results in ejaculatory-like responses", Neuroscience 2012, 690.16/WW5, 2012, Abstract, 2 pages.

International Search Report and Written Opinion issued Oct. 18, 2016 in PCT/JP2016/003301 (submitting English translation only).

Y. Kimura, et al., "894 A Novel Therapeutic Strategy for Patients with Premature Ejaculation: Possibility of Electrical Stimulation of Dorsal Penile Nerves", European Urology Supplements, vol. 15, No. 3, Published Mar. 11, 2016, p. e894 (submitting English Abstract only).

Y. Kimura, et al., "894 A Novel Therapeutic Strategy for Patients with Premature Ejaculation: Possibility of Electrical Stimulation of Dorsal Penile Nerves", Poster, Standard Poster and ePoseter presented on the 31st Annual European Association of Urology Congress, Munich, Mar. 11-15, 2016, 15 Pages.

* cited by examiner

FIG. 5
(a) URETHRAL PERFUSION PRESSURE (UPP)
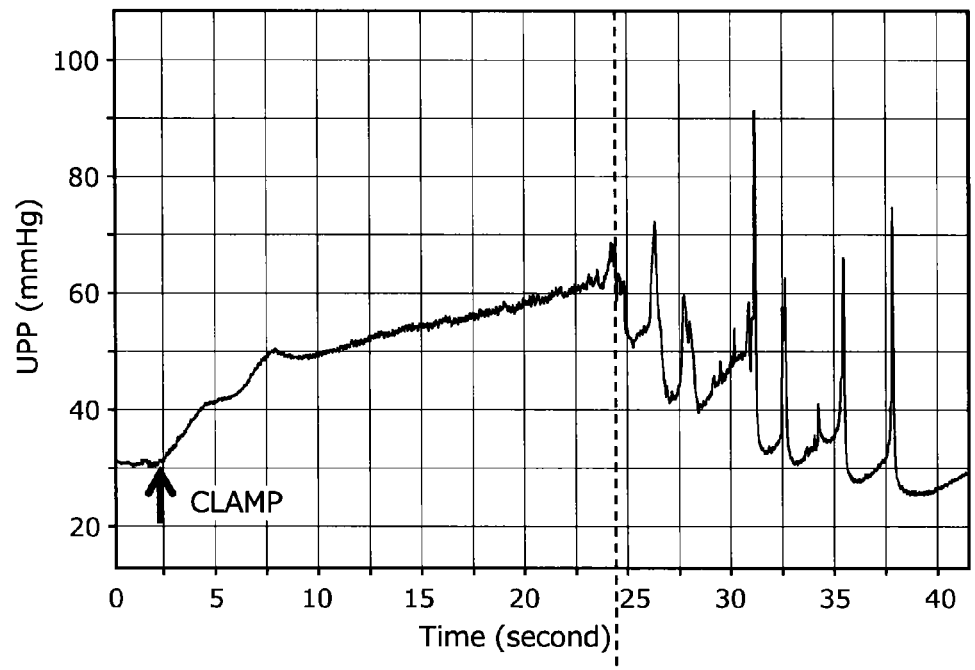
(b) BULBOSPONGIOSUS MUSCLE
ELECTROMYOGRAM (BSM-EMG)
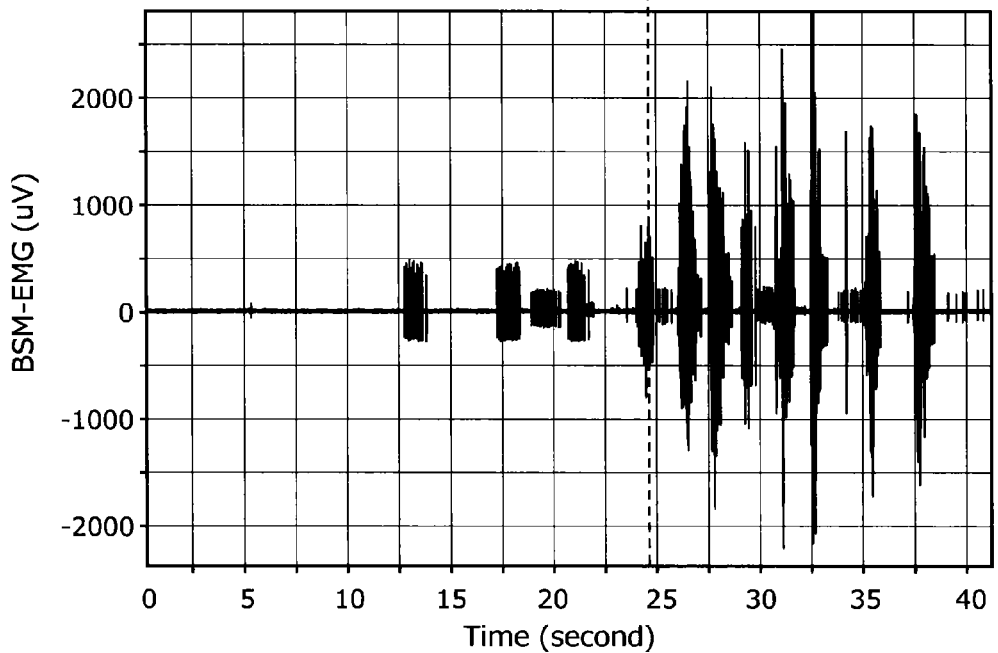

FIG. 6
(a) URETHRAL PERFUSION PRESSURE (UPP)
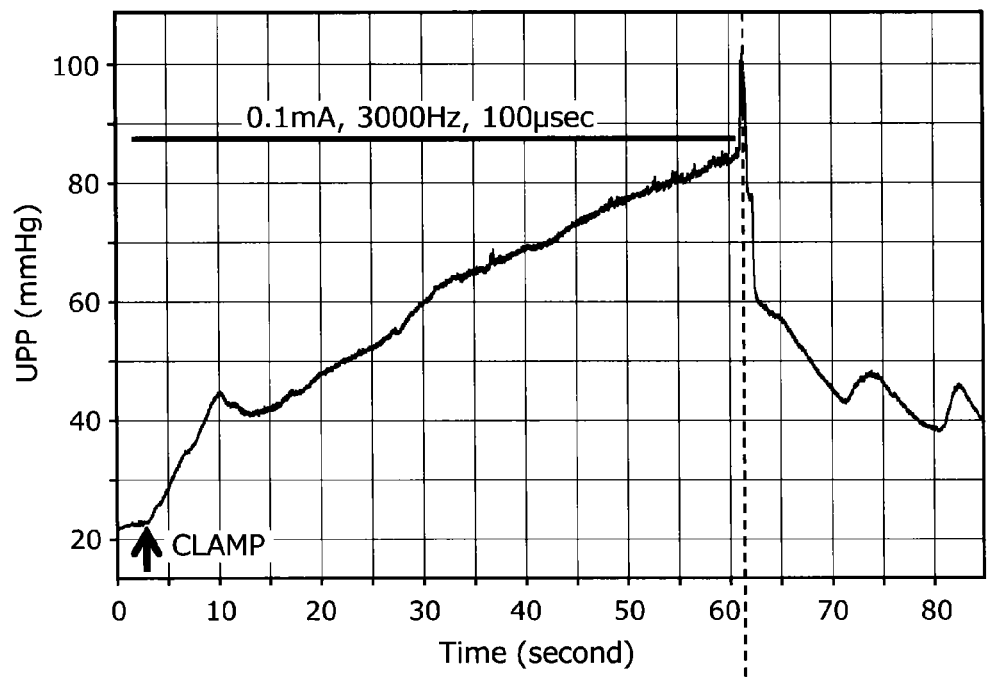
(b) BULBOSPONGIOSUS MUSCLE ELECTROMYOGRAM (BSM-EMG)
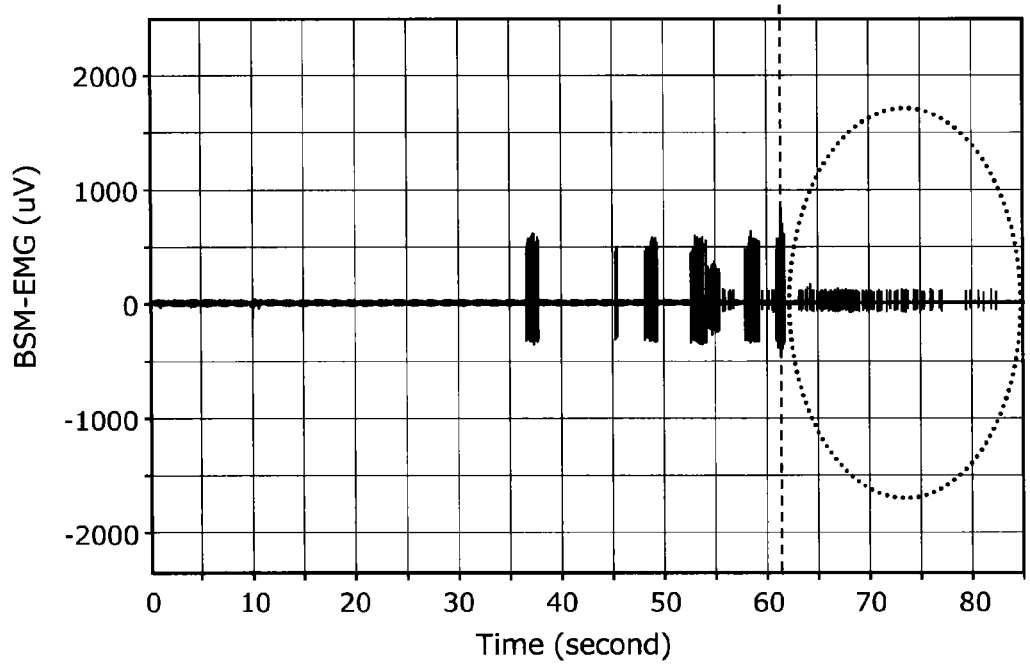

METHOD FOR TREATING PREMATURE EJACULATION AND METHOD FOR CONTROLLING PREMATURE EJACULATION TREATMENT DEVICE

BACKGROUND OF THE INVENTION

Field of the Invention

The present invention relates to methods for treating premature ejaculation and methods for controlling a premature ejaculation treatment device.

Discussion of the Background

Ejaculatory dysfunction is a class of male sexual disorders, which includes premature or rapid ejaculation, delayed ejaculation, complete inability to ejaculate, retrograde ejaculation, painful ejaculation, and the like. Among them, premature ejaculation is the most common ejaculatory dysfunction, and reportedly affects 5-40% of sexually active men (Nature Clinical Practice Urology, 5: 93-103, 2008). Premature ejaculation is a male sexual disorder characterized by ejaculation that always or nearly always occurs prior to or within about 1 min of vaginal penetration from the first sexual experience (life-long premature ejaculation), a clinically significant reduction in intravaginal ejaculatory latency time (IELT), often to about 3 minutes or less, during sexual intercourse (acquired premature ejaculation), the inability to delay ejaculation in all or nearly all vaginal penetrations, and negative personal consequences, such as distress, bother, frustration, and/or the avoidance of sexual intimacy (Journal of Sexual Medicine, 11: 1392-1422, 2014).

As treatment options for premature ejaculation, pharmacologic, psychological, and behavioral therapies are known. As pharmacological agents for treating premature ejaculation, topical anesthetic agents directly applied to the glans of the penis and oral agents such as tricyclic antidepressants and selective serotonin reuptake inhibitors (SSRIs) have been used (Journal of Sexual Medicine, 3: Suppl 4, 309-317, 2006; Journal of Sexual Medicine, 11: 1392-1422, 2014).

However, the topical anesthetic agents directly applied to the glans of the penis cause penile hypoesthesia, transvaginal contamination, and female genital anesthesia. Further, the anesthetic agents must be applied to the penis right before sexual intercourse, making such agents less convenient.

The oral agents may cause systemic adverse effects such as nausea, diarrhea, insomnia, and the like, while the antidepressants bring about concerns over change in mental condition. Further, there is concern that SSRIs may be associated with spermatogenesis hypofunction (F1000Prime reports, 6: 55, 2014).

It has been reported that behavioral and psychological therapies may work only for a short period of time with low efficiency (Nature Clinical Practice Urology, 5: 93-103, 2008; F1000Prime Reports, 6: 55, 2014).

There are several reports suggesting that patients with premature ejaculation have penile hypersensitivity (The Journal of Urology, 156: 979-981, 1996; The Journal of Urology, 158: 451-455, 1997; Urology, 11: 81-82, 1978). Further, there is a report indicating that the number of dorsal penile nerves (DPNs) in patients with premature ejaculation is greater than in healthy persons (Chinese Medical Journal, 122: 3017-3019, 2009). Based on these observations, a method called selective resection of DPNs, in which roughly half of the distributed DPNs of a patient with premature ejaculation are selectively resected (International Journal of Andrology, 35: 873-879, 2012), and a method in which CT-guided unilateral cryoablation is performed on DPNs (Journal of Vascular and Interventional Radiology, 24: 214-219, 2013), have been proposed to improve short IELT.

These methods, in which some DPNs are resected can indeed extend IELT. However, because such operations are irreversible, it is impossible to modify IELT after the operation—even if IELT ends up being longer than desired or needs to be shortened.

Further, a method of extending IELT of patients with premature ejaculation using pulsed radiofrequency (PRF) has been proposed (Journal of Andrology, 31: 126-130, 2010 (Basel et al)). PRF was performed on the right and left DPNs with an impedance setting of 200-450 ohms and a radiofrequency generator output setting of 2×20 ms/s and 45 V at 42° C. for 180 sec. As a result, IELT of patients was extended from 18.5±17.9 to 139.9±55.1 sec three weeks after the procedure.

Furthermore, sexual satisfaction scores for the patients and their partners were significantly improved three weeks after the procedure when compared with sexual satisfaction scores before the procedures. Although IELT was not evaluated in a follow-up period after the period of three weeks after the procedure, none of the patients or their partners reported any treatment failure during the follow-up period; the mean follow-up period was 8.3±1.9 months.

The above result indicates that the effect of PRF can be maintained for at least about 8.3 months with a single procedure, leading to speculation that the effect of this procedure may have resulted from a structural change in DPNs.

In Basel et al, it was asserted that PRF neuromodulation has recently been described as an alternative technique to resection of nerves, in which relatively high voltage is applied near nerves without nerve injury. However, citation is made to Pain, 73: 159-163, 1997 (Slappendel et al), which indicates that PRF neuromodulation performed for 90 sec at 67° C. and for 90 sec at 40° C. may cause nerve damage and neuritis as adverse effects.

PRF neuromodulation conditions in Basel were 42° C./180 sec, which includes a higher procedure temperature and longer procedure time than the 40° C./90 sec conditions employed in Slappendel et al. Combining this with the fact that the effect of the procedures in Basel lasted for as long as 8.3 months, it is reasonable to conclude that the effect of extending IELT in the procedure performed in Basel was caused by structural change to the nerves.

As explained above, the procedure of using PRF on DPNs described in Basel is an irreversible operation that causes structural change to DPNs. Thus, similar to nerve resection, IELT is not adjustable after PRF procedures are performed on DPNs.

As such, there is no known procedure for treating premature ejaculation that exerts its effect only when needed, does not result in systemic adverse effects, and does not rely on irreversible operations such as nerve resection or nerve injury, in which nerves cannot recover after the operation is performed.

BRIEF SUMMARY OF THE INVENTION

In various exemplary embodiments of the present invention, the above-described long-felt need is addressed by exemplary methods for treating premature ejaculation and exemplary methods for controlling a premature ejaculation treatment device. The methods are convenient and reversible, and the methods improve IELT in patients with premature ejaculation without systemic adverse effects or impacts on their partners.

Various exemplary embodiments of the present invention are directed to a method of treating premature ejaculation, including arranging one or more electrodes to face DPNs of a patient with premature ejaculation, and applying an electro stimulation having a frequency and a current by which seminal fluid expulsion is not induced in the patient by the one or more electrodes during a time period from before the start of sexual intercourse to ejaculation. In embodiments, the electro stimulation reversibly extends an IELT of the patient.

In some such embodiments, the frequency of the electro stimulation is 100-5,000 Hz.

In some such embodiments, arranging one or more electrodes comprises implanting one or more electrodes surgically under skin at a proximal portion of the penis of the patient in contact with DPNs.

In some such embodiments, arranging one or more electrodes comprises arranging one or more electrodes to face less than all DPNs of the patient.

In some such embodiments, applying the electro stimulation comprises applying the electro stimulation for a period of time that does not exceed 60 minutes per day.

Various exemplary embodiments of the present invention are directed to a method of controlling a premature ejaculation treatment device for extending IELT of a patient with premature ejaculation. In embodiments, the device includes an intracorporeal device including one or more electrodes implanted into a proximal portion of the penis of the patient in contact with DPNs and a stimulation setting device disposed outside the body of the patient for outputting to the intracorporeal device a control signal for controlling an electro stimulation applied by the electrodes. In embodiments, the method is performed in the intracorporeal device and includes receiving from the stimulation setting device information designating timing for the electro stimulation by the electrodes, and a frequency, a current, and a duration of the electro stimulation by which seminal fluid expulsion is not induced in the patient, determining if the timing for the electro stimulation has been reached, and applying the electro stimulation having the designated frequency and current for the designated duration by outputting the information to the electrode when it is determined that the timing for the electro stimulation has been reached.

In some such embodiments, the designated frequency of the electro stimulation is 100-5,000 Hz.

In some such embodiments, the premature ejaculation treatment device further includes a timing command device for sending a command designating the timing for the electro stimulation to the intracorporeal device by operation by the patient. In some such embodiments, determining if the timing for the electro stimulation timing is reached comprises determining if the timing for the electro stimulation is reached based on the command received from the timing command device.

BRIEF DESCRIPTION OF THE FIGURES

A more complete appreciation of the invention and many of the attendant advantages thereof will be readily obtained as the same become better understood by reference to the following detailed description when considered in connection with the accompanying drawings, wherein:

FIG. 5 is a graph showing exemplary changes in measurement values of urethral perfusion pressure (UPP) and bulbospongiosus muscle-electromyogram (BSM-EMG) in a preset value acquisition session using the UGR model;

FIG. 6 is a graph showing exemplary changes in measurement values of UPP and BSM-EMG in an electro stimulation session with parameter values of 0.1 mA, 3,000 Hz, and 100 μsec using the UGR model.

DETAILED DESCRIPTION OF THE INVENTION

Figure 1:
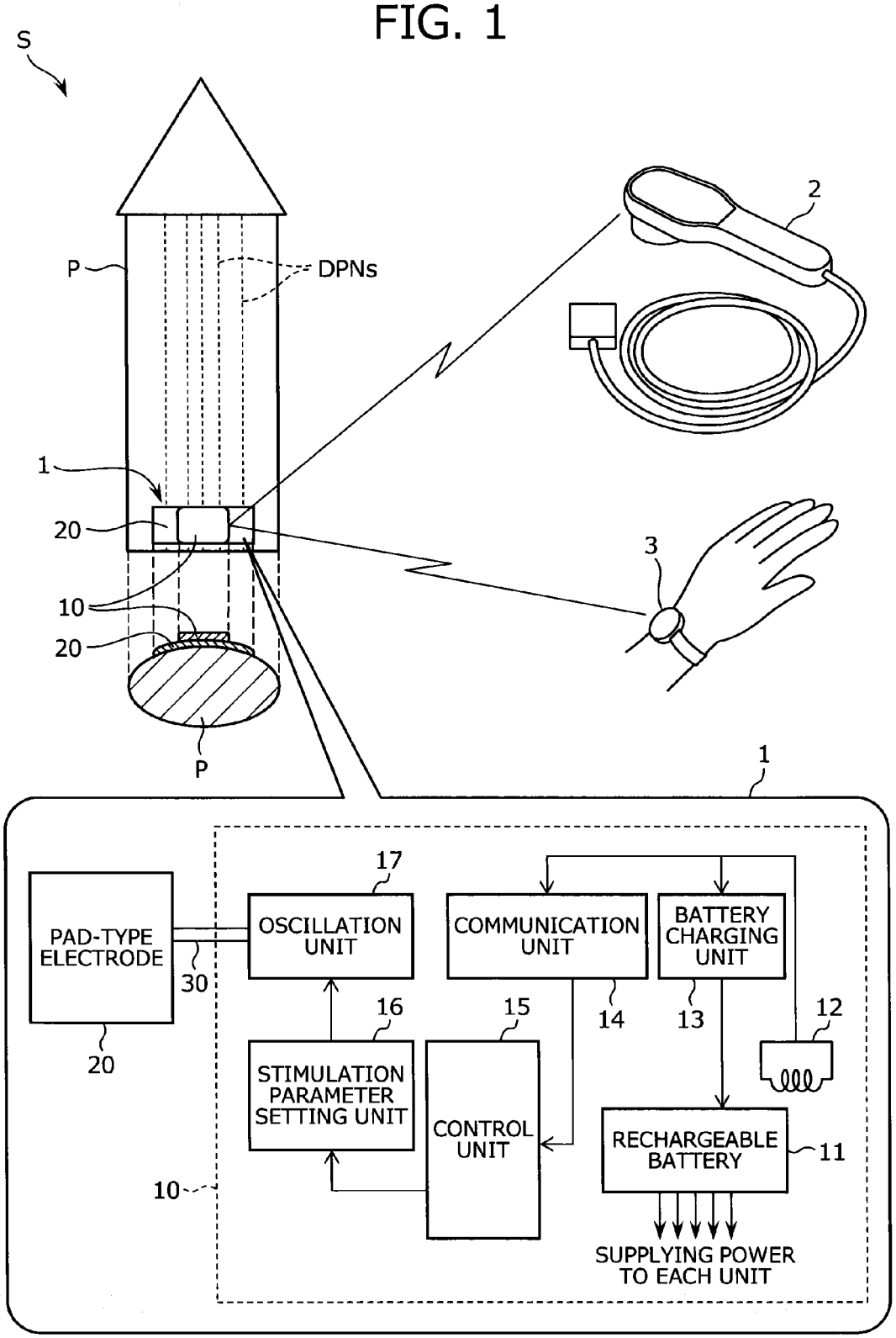
FIG. 1 is a diagrammatic illustration of an exemplary premature ejaculation treatment device according to the present invention.

Exemplary methods for treating premature ejaculation and exemplary methods for controlling a premature ejaculation treatment device according to the present invention are excellent in convenience and are reversible. Such exemplary methods improve IELT in patients with premature ejaculation without systemic adverse effects or impacts on their partners.

Various exemplary embodiments of the present invention are directed to a method of treating premature ejaculation including applying an electro stimulation to DPNs of a patient suffering from premature ejaculation under conditions that reversibly increase an IELT of the patient measured prior to treatment.

Various exemplary embodiments of the present invention are directed to a method of treating premature ejaculation including applying an electro stimulation to DPNs of a patient suffering from premature ejaculation under conditions that increase an IELT of the patient measured prior to treatment, the electro stimulation being applied prior to or during each of multiple instances of intercourse.

In some such embodiments, applying the electro stimulation includes applying the electro stimulation for a period of time and at a current and frequency sufficient to increase an amount of penile stimulation during sexual intercourse required to achieve seminal fluid expulsion by the patient relative to the amount of stimulation required prior to treatment.

In some such embodiments, applying the electro stimulation includes applying the electro stimulation at a frequency in a range of from 100 to 5,000 Hz.

In some such embodiments, the method includes adhering a device externally to the body of the patient so that the device faces DPNs of the patient, and applying an electro stimulation to DPNs of the patient via the device.

In some such embodiments, adhering the device externally to the body includes wrapping a cuff including the device around the penis of the patient.

In some such embodiments, adhering the device externally to the body includes positioning the device so that it faces some but not all of the DPNs of the patient.

In some such embodiments, applying the electro stimulation includes initiating the electro stimulation by actuating a switch.

In some such embodiments, the switch is provided on a second device remote from the device adhered externally to the body of the patient.

Various exemplary embodiments of the present invention are directed to a method of treating premature ejaculation. In embodiments, the method includes implanting a device into a patient suffering from premature ejaculation. In embodiments, the device is surgically implanted in the body of the patient so that the device faces DPNs of the patient, and the device is capable of applying electro stimulation to DPNs under conditions that reversibly increase an IELT of the patient measured prior to treatment.

In some such embodiments, implanting the device into the patient includes positioning the device so that the device faces some but not all of the DPNs of the patient.

In some such embodiments, the method further includes inputting information to the device designating at least one of a minimum period of time between applications of the electro stimulation, a period of duration of the electro stimulation, a current of the electro stimulation, and a frequency of the electro stimulation, to be carried out by the device when activated by the patient.

In some such embodiments, inputting information to the device includes inputting information with a second device remote from the device implanted into the patient.

In some such embodiments, inputting information to the device includes inputting information specifying that electro stimulation at a frequency in a range of from 100 to 5,000 Hz is to be carried out by the device when activated by the patient.

Various exemplary embodiments of the present invention are directed to a method for controlling a premature ejaculation treatment device. In embodiments, the device is implanted into a proximal portion of the penis of a patient requiring treatment. In embodiments, the device includes at least one electrode facing DPNs of the patient. In embodiments, the device is capable of administering an electrostimulation to the DPNs under conditions that reversibly increase an IELT of the patient measured prior to treatment. In embodiments, the device includes memory including information designating a minimum period of time between applications of the electro stimulation, and at least one of a period of duration of the electro stimulation, a current of the electro stimulation, and a frequency of the electro stimulation. In embodiments, the method includes receiving information instructing the device to begin the electro stimulation, determining whether the minimum period of time between applications of the electro stimulation has elapsed, and, if it is determined that the minimum period of time between applications of the electro stimulation has elapsed, applying the electro stimulation having at least one of the designated period of duration, current, and frequency.

In some such embodiments, receiving information instructing the device to begin the electro stimulation includes receiving information transmitted by a second device remote from the device implanted into the patient. In embodiments, the information is transmitted by the second device when the patient actuates a switch.

Various exemplary embodiments of the present invention are directed to a method for controlling a premature ejaculation treatment device. In embodiments, the device is implanted into a proximal portion of the penis of a patient requiring treatment. In embodiments, the device includes at least one electrode facing DPNs of the patient. In embodiments, the device is capable of administering an electro stimulation to the DPNs under conditions that reversibly increase an IELT of the patient measured prior to treatment. In embodiments, the device includes a memory. In embodiments, the method includes transmitting information designating a minimum period of time between applications of the electro stimulation, and at least one of a period of duration of the electro stimulation, a current of the electro stimulation, and a frequency of the electro stimulation to the device.

In some such embodiments, transmitting information includes transmitting information from a second device remote from the device implanted into the patient.

An ejaculatory phenomenon consists of two phases, namely the emission phase, where seminal fluid discharged from the ejaculatory duct and mixed with prostatic fluid is released into the posterior urethra, and the expulsion phase, where the seminal fluid released into the posterior urethra is ejected outside the body through several rhythmic contractions of the external sphincter, bulbospongiosus muscle (BSM), and ischiospongiosus muscle. Penile stimulation is transmitted via DPNs, a branch of the pudendal nerves, to the ejaculation center in the spinal cord, from which efferent signals are sent out mostly via the lumbar splanchnic nerves to the seminal tract to induce ejaculation. It is generally believed that spinal reflex is further regulated by a supraspinal center, especially medial preoptic area in hypothalamus.

There are many reports describing that electro stimulation of DPNs elicits an ejaculation-like response in rats and human (Journal of Urology, 149: 627-632, 1993; Journal of Sexual Medicine, 7:2445-2457, 2010; Journal of Sexual Medicine, 9:1303-1318, 2012; BJU International, 85: 857-863, 2000). Further, penile stimulation treatment using a vibrator has been performed in patients with ejaculatory dysfunction to induce ejaculation (International Journal of Andrology, 25: 324-332, 2002; Urology, 69: 552-556, 2007; Urology, 55: 915-917, 2000). Thus, the idea that stimulation of DPNs elicits the ejaculatory response has been accepted as common knowledge. However, the present inventors discovered that, surprisingly and contrary to accepted wisdom, electro stimulation of DPNs negatively regulates the ejaculatory response under certain conditions.

In various exemplary embodiments, the devices and methods of the present invention make it possible to extend IELT of patients with premature ejaculation by electrically stimulating DPNs of the patients using an electrical signal having a frequency and current by which ejaculation is not induced. Thus, input of an afferent signal from the penis into the ejaculation center is suppressed.

Various exemplary embodiments of the present invention are directed to a method for treating premature ejaculation, which extends IELT of a patient with premature ejaculation. In embodiments, the method includes arranging one or more electrodes to face DPNs of a patient, and applying an electro stimulation signal from the electrodes having frequency and current by which seminal fluid expulsion is not induced in the patients during the time period from before the start of sexual intercourse to ejaculation.

As the input from DPNs is inhibited by such configuration, IELT of the patient is extended, thereby sexual satisfaction of the patient as well as his partner is improved.

Various exemplary embodiments of the present invention are directed to a method for controlling a premature ejaculation treatment device. In embodiments, the premature ejaculation treatment device extends IELT of a patient with premature ejaculation and includes an intracorporeal device having one or more electrodes implanted into the proximal portion of the penis to contact with the DPNs of the patient and a stimulation setting device disposed outside the body for outputting a control signal for electro stimulation applied by the electrodes to the intracorporeal device. In embodiments, the method is performed in the intracorporeal device, and includes receiving an information for designating the electro stimulation timing by the electrodes and frequency, current, and duration of the electro stimulation by which seminal fluid expulsion is not induced from the stimulation setting device, determining if the electro stimulation timing is reached, and applying the electro stimulation having the designated frequency and current for the designated duration by outputting the information for designating the frequency, the current, and the duration to the electrode when it is determined that the electro stimulation timing is reached.

In embodiments of the method for controlling a premature ejaculation treatment device, the frequency of the electro stimulation may be set at 100-5,000 Hz.

In embodiments of the method for controlling a premature ejaculation treatment device, arranging the electrodes may include implanting the electrodes surgically under the skin at the proximal portion of the penis of the patient to contact with DPNs.

In such a configuration, unlike a configuration in which an electrode is disposed outside of the body, it is not necessary to put the electrode on the penis during each instance of sexual intercourse, thus improving convenience for the patient.

In embodiments of the method for controlling a premature ejaculation treatment device, arranging the electrodes includes arranging the electrodes to face some of a plurality of DPNs, but not the rest of them.

Such a configuration does not completely block all neural transmission in DPNs of the patient with premature ejaculation, and the activity of pulse transmission in DPNs can partially remain. Thus, suppression of seminal fluid expulsion becomes possible by allowing the patient to control the timing of the seminal fluid expulsion by his own volition. It is further possible to adjust an effect achieved by devices and methods of the present invention by incrementally changing the number of the DPNs to be treated from one to the whole quantity depending on the degree of premature ejaculation symptom of the patient.

In embodiments, applying electro stimulation may include applying the electro stimulation so that total electro stimulation time per day does not exceed 60 min.

Employing such a limitation can prevent DPNs from being damaged.

In embodiments, the premature ejaculation treatment device or system according to the present invention may further include a timing command device for sending a command for designating the electro stimulation timing to the intracorporeal device corresponding to the operation by the patient. In embodiments, determining if the electro stimulation timing is reached may include determining if the electro stimulation timing is reached based on the command received from the timing command device.

A device having such a configuration allows a doctor to set up a profile of the electro stimulation using a stimulation setting device, and the patient to determine the timing of the electro stimulation using the timing command device, thus enabling the electro stimulation to be performed at a time convenient to the patient under the appropriate conditions complying with the doctor's guidance, which can increase the effectiveness of the treatment, and inhibit systemic adverse effects.

Various exemplary embodiments of the devices and methods according to the present invention will be described hereinafter with reference to FIGS. 1 to 7.

"IELT" as used herein is defined as the time between the start of vaginal intromission and seminal fluid expulsion in sexual intercourse.

Further, the methods for treating premature ejaculation and the methods for controlling the premature ejaculation treatment device of the present invention are described in the context of a human patient with premature ejaculation. However the present invention is not limited thereto, and may be applied to animals such as the animals in zoos and farms, to pets, to designated endangered species, and the like, for the purposes of infertility treatment and propagation.

Method for Treating Premature Ejaculation

In various exemplary embodiments, the method for treating premature ejaculation according to the present invention is a method for extending IELT of a patient with premature ejaculation by applying an electro stimulation from an electrode to DPNs of the patient with premature ejaculation. In embodiments, the electro stimulation is provided during a time period from before sexual intercourse to ejaculation, especially from vaginal intromission to seminal fluid expulsion. In embodiments, the electro stimulation suppresses input of an afferent signal from the DPNs into the ejaculation center during sexual intercourse. Herein, "from vaginal intromission" includes the following time points as starting points: at the same time as vaginal intromission, right before and after vaginal intromission, and before and after vaginal intromission.

Further, "before sexual intercourse" includes a preparation period as well as a preceding period of sexual intercourse.

In embodiments, the electro stimulation applied to DPNs is performed at a current and frequency that inhibits, suppresses, or prevents seminal fluid expulsion. Inhibition, suppression, or prevention may constitute less than complete inhibition, suppression, or prevention. That is, the electro stimulation may have the effect of increasing the amount of stimulation (e.g., duration of stimulation) required to achieve seminal fluid expulsion relative to the amount of stimulation required prior to treatment, thus delaying rather than preventing seminal fluid expulsion. An exemplary frequency that inhibits seminal fluid expulsion is 100-5,000 Hz. In embodiments, the effect of the method for treating premature ejaculation of the present invention is adjusted by controlling the current and frequency of the electro stimulation. Although the current that inhibits seminal fluid expulsion is adjustable in various ranges, the value may be set, for example, below a value at which seminal fluid expulsion is induced.

In embodiments, the electro stimulation applied to DPNs is performed at a current and frequency at which seminal fluid expulsion is inhibited, and the current and frequency is maintained continuously after vaginal intromission of the penis so as to cover the period during which thrust stimulation is being input into the DPNs. In embodiments, the duration of the electro stimulation is longer than IELT a patient shows before the treatment, but the same or shorter than IELT in the normal range (3-10 min, ideally about 6 min). Although the electro stimulation is continuously applied to DPNs in this embodiment, the present invention is not limited thereto, and the electro stimulation may also be intermittently applied.

Further, the electro stimulation may be applied to all or some of the plurality of DPNs.

In embodiments, electro stimulation is applied to DPNs of a patient under conditions that reversibly increase an IELT of the patient measured prior to treatment. That is, if electro stimulation is discontinued, the patient's IELT will decrease. The period of time for reversal or decrease of the patient's IELT after ceasing electro stimulation may be, for example, one hour, a few hours, half a day, or one day. Decreasing the patient's IELT may mean a return to the IELT of the patient measured prior to treatment, but also may mean a decrease of the IELT of the patient relative to the IELT achieved during treatment. Thus, by applying electro stimulation to DPNs of the patient under the conditions described above, it is possible to achieve impermanent treatment, which can be modified, e.g., if initial selected conditions result in an IELT that is undesirably long.

Premature Ejaculation Treating Device and Control Method Thereof

FIG. 1 shows an exemplary embodiment of a premature ejaculation treatment device S used in an exemplary method for treating premature ejaculation according to the present invention. The premature ejaculation treatment device S is an implantable electro stimulation device, and extends IELT of a patient with premature ejaculation to a time that the patient desires, i.e. longer than IELT the patient showed before treatment, or within the normal range of time (3-10 min, ideally about 6 min).

The premature ejaculation treatment device S includes an electro stimulation device 1 implanted into the proximal portion of the penis P of the patient, where DPNs are concentrated, a programming wand 2 for wirelessly transmitting a program carrying an electro stimulation profile to the electro stimulation device 1 from the outside of the body of the patient, and a switch 3 for performing on/off control of the electro stimulation applied from the electro stimulation device 1 from the outside of the body.

In this embodiment, the electro stimulation device 1 is implanted inside the body of the patient. However, the present invention is not limited thereto, and a small external electro stimulation device may be adhered by an adhesive plaster to face DPNs in the proximal portion of the penis P, or a small external electro stimulation device may be wrapped around the penis P through a thin cuff which has the device attached to the inner surface thereof. Further, if the proximal portion of the penis P is not an ideal location for implantation in some patients, the device may be arranged on other parts of the penis P, or on pudendal nerves proximal to DPNs. The programming wand 2 may be shared by a plurality of patients, in which each programming wand has an identical function or multiple wands may have divided functions that mutually complete one another.

The electro stimulation device 1 constitutes an all-in-one device, which comprises a pad-type electrode 20 for applying the electro stimulation to the DPNs, a generator 10 for controlling the pad-type electrode 20 and performing transmission/reception of information with the programming wand 2 and the switch 3, a lead wire 30 for connecting between the pad-type electrode 20 and the generator 10, and a rechargeable battery 11.

Although, in this embodiment, the electro stimulation device 1 is an all-in-one device, where the pad-type electrode 20, the generator 10, the lead wire 30, and the rechargeable battery 11 are integrally formed, the electro stimulation device 1 may be configured in a separated arrangement, where the pad-type electrode 20 and the generator 10 are located separately. In the separated arrangement, the pad-type electrode 20 is arranged on the proximal portion of the penis P as seen in FIG. 1, the generator 10 is implanted inside the body but outside the penis P, and the pad-type electrode 20 and the generator 10 are connected with the lead wire 30 consisting of a long wire. Further, other types of electrodes, such as a cuff electrode of a wrapping type, may also be used instead of the pad-type electrode. Exemplary generators that may be used as the generator 10 of the electro stimulation device 1 include VNS Therapy generators marketed and sold by Cyberonics, Inc., of Houston, Tex. Cyberonics Demipulse® and Demipulse Duo® Generators are exemplary implantable, programmable pulse generators that deliver a pattern of electro stimulation.

In embodiments, the pad-type electrode 20 is a known implantable electrode made of a metal material, such as platinum and platinum alloy, which exhibits conductivity and biocompatibility. Parts of the lead wire 30 and the pad-type electrode 20 are covered with other biocompatible materials, such as silicone, to achieve biocompatibility. The length of the pad-type electrode 20 in the circumferential direction of the penis P is preferably 2.5 cm or more in order to cover all the necessary DPNs. For example, the pad-type electrode 20 may have a length of about 2.5 cm in the circumferential direction of the penis, a length of about 0.5 cm in the longitudinal direction of the penis, and a thickness of about 0.2 cm. In this case, the generator 10 may have, for example, a length of about 1.0 cm in the circumferential direction of the penis, a length of about 0.5 cm in the longitudinal direction of the penis, and a thickness of about 0.3 cm.

In embodiments, the electro stimulation device 1 is implanted inside the penis P in such a way that the pad-type electrode 20 is contacted with some or all of the plurality of DPNs of the penis P of the patient. Since there is a plurality of DPNs in the penis P, the pad-type electrode 20 may be arranged to contact some DPNs, but not contact the rest of them. By leaving some DPNs uncontacted with the pad-type electrode 20, only a portion of the plurality of DPNs receives a seminal fluid expulsion suppression effect from the pad-type electrode 20, while the rest of the plurality of DPNs does not receive the suppression effect. In this way, seminal fluid expulsion during sexual intercourse is not completely suppressed, thus it becomes possible to control the timing of seminal fluid expulsion in a manner reflecting the intention of the patient.

In embodiments, the generator 10 functions to receive and store the program carrying the electro stimulation profile sent from the programming wand 2 outside the body, and instruct the pad-type electrode 20 to generate an electro stimulation signal according to the electro stimulation profile when a command is received from the switch 3 outside the body.

In embodiments, the generator 10 comprises a circuit board, which includes, as shown in FIG. 1, the rechargeable battery 11, a coil unit 12, a battery charging unit 13, a communication unit 14, a control unit 15 including a microcomputer, etc., a memory section (not illustrated), a stimulation parameter setting unit 16, and an oscillation unit 17. The generator 10 may comprise hardware units, software units, firmware units, or any combination thereof. One or more blocks illustrated in FIG. 1 may be combined with other blocks, which may represent circuit hardware units, software algorithms, etc. Additionally, any number of the circuitry or software units associated with the various blocks illustrated in FIG. 1 may be combined into a programmable device, such as a field programmable gate array, an ASIC device, etc.

The rechargeable battery 11 comprises, for example, a lithium ion battery. The coil unit 12 may be a coil. The coil may be a resonance circuit including, for example, a coil and a capacitor. The coil may receive an electromagnetic wave for charging a battery sent from the programming wand 2 outside the body. An AC current generated in the coil unit 12 upon the reception of the electromagnetic wave may be output to the battery charging unit 13. Further, the coil unit 12 may receive an electromagnetic wave carrying the electro stimulation profile sent from the programming wand 2 outside the body, and output the received electromagnetic wave to the communication unit 14.

The battery charging unit 13 may be a battery charger. The battery charger may include a built-in rectifying circuit that converts the AC current output from the coil unit 12 to a DC current to acquire power, and charges the rechargeable battery 11.

The communication unit 14 may demodulate the electromagnetic wave received by the coil unit 12, extract the electro stimulation profile carried in the electromagnetic wave, and store the extracted electro stimulation profile at the memory section (not illustrated). The communication unit may be a communicator including hardware, software, firmware, or any combination thereof. The memory section (not illustrated) may be a memory including one or more of random access memory (RAM), dynamic random access memory (DRAM), electrically erasable programmable read-only memory (EEPROM), flash memory, etc.

The stored electro stimulation profile at the memory section (not illustrated) may be output to the stimulation parameter setting unit 16 through the control of the control unit 15, triggered by the reception of an ON signal from the switch 3. The electro stimulation profile may be a signal that defines values of voltage, current, frequency, duration, and the like. The control unit 15 may be a controller. The controller may include various components, such as a processor, a memory, etc. The processor may include one or more microcontrollers, microprocessors, etc., capable of performing various executions of software components.

The stimulation parameter setting unit 16 may generate a stimulation intensity modifying signal for modifying stimulation intensity of the electro stimulation signal generated in the oscillation unit 17, based on the electro stimulation profile input from the communication unit 14 via the memory section (not illustrated), and output the stimulation intensity modifying signal to the oscillation unit 17. The stimulation parameter setting unit 16 may include various components, such as a processor, a memory, etc., capable of performing various executions of software components.

The oscillation unit 17 may generate the electro stimulation signal based on the stimulation intensity modifying signal input from the stimulation parameter setting unit 16, and output the electro stimulation signal to the pad-type electrode 20. The electro stimulation signal may be determined by the values of voltage, current, frequency, duration, and the like. The oscillation unit 17 may be an oscillator, such as a crystal oscillator.

The rechargeable battery 11 shown in FIG. 1 is installed in the generator 10, and the generator 10 is covered with a biocompatible material, such as titanium and the like to achieve biocompatibility.

The programming wand 2 may be an information communication device for a doctor to operate, and may include a CPU, a memory section, and an information transmission/reception section. In embodiments, the programming wand 2 is a specialized apparatus having only a setting function for electro stimulation conditions. However, the programming wand 2 may also have other functions in a single device. Although the programming wand 2 is formed in a wand-like shape for easy operation by a doctor in FIG. 1, the programming wand 2 may also be formed in other shapes, such as a plate-like shape. Alternatively, information terminals, such as tablet terminals, smartphones, media players, and personal computers may be used as the programming wand 2.

The programming wand 2 may send the electro stimulation program that determines the electro stimulation profile for the pad-type electrode 20 to the generator 10. In embodiments, the electro stimulation program can be modified only by a doctor or a person having permission from the doctor. The programming wand 2 may also include a wireless switch to perform ON/OFF control over the electro stimulation device 1 in order to allow the doctor to conduct a performance test on the electro stimulation device 1. Exemplary devices that may be used as the programming wand 2 include Programming Wands marketed and sold by Cyberonics, Inc., of Houston, Tex. Cyberonics Model 201 Programming Wand is an exemplary programming wand that can store and retrieve telemetry data and revise programmable parameters in a generator.

The switch 3 is a wristwatch type switch in FIG. 1. In embodiments, the switch is a short-range wireless communication device having a short-range communication area of about several centimeters to several meters. As a system for the short-range radio communication, a variety of systems, such as near field communication (NFC), Bluetooth (registered trademark), and RFID (radio frequency identifier) may be used.

The switch 3 may include an ON/OFF switch (not illustrated) for switching on or off the generator 10 by sending an on signal or an off signal to the generator 10, and a transmission unit (not illustrated) for wirelessly transmitting a command issued by an input from the ON/OFF switch, and may be configured to turn on and off a power of the generator 10 through the operation of the ON/OFF switch within a communication area of the generator 10.

Once a doctor sends an electro stimulation program from the programming wand 2 to the generator 10, and sets up the electro stimulation profile in the generator 10, a patient wearing the switch 3 on his wrist makes the ON/OFF operation according to the doctor's instruction, and sends the on signal or the off signal to the generator 10. As a result, the electro stimulation can be applied to DPNs under conditions suitable for the patient.

In the embodiment shown in FIG. 1, the switch 3 is a wristwatch type switch. However, the shape of the switch 3 is not limited thereto, and the switch 3 may have any form, including a necklace-type switch, a pierced earring-type switch, an ear hook-type switch, a finger ring-type switch, a tattoo sticker-type switch, and an artificial nail-type switch, as long as the switch 3 is wearable by the patient.

Implantation of the electro stimulation device 1 is, for example, performed as follows. First, the skin of the proximal dorsal portion of the penis P is dissected, and lipids, connective tissues, and the like are removed until the DPNs are confirmed. The electro stimulation device 1 is placed on the confirmed DPNs, and both ends of the pad-type electrode 20 are joined to and tightly fixed to the penis. Finally, the skin is sutured to complete the implantation of the electro stimulation device 1.

Next, an exemplary embodiment of the electro stimulation processing according to the present invention is explained, in which the electro stimulation having a profile set up by the doctor with the programming wand 2 is applied from the electro stimulation device 1 through the patient's operation of the switch 3.

First, the doctor sets up the electro stimulation profile using the programming wand 2.

When the doctor clicks an electro stimulation setting program icon on a screen of the programming wand 2, a CPU (not illustrated) of the programming wand 2 starts to process the electro stimulation setting program. This processing is executed by the CPU (not illustrated) of the programming wand 2 as well.

Figure 3:
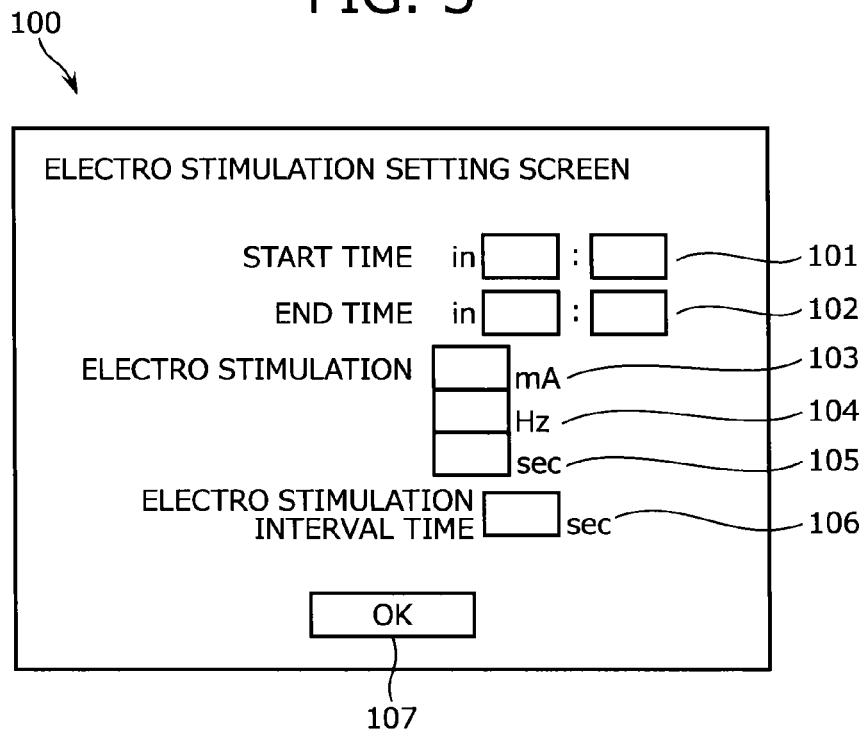
FIG. 3 is a schematic view of an electro stimulation setting screen of an exemplary premature ejaculation treatment device according to the present invention.

The screen first displays an electro stimulation setting screen 100 in FIG. 3 for setting up an electro stimulation condition for the penis P. The electro stimulation setting screen 100 in FIG. 3 includes a start time input column 101 for the electro stimulation of the penis P, an end time input column 102 for the electro stimulation, a current value input column 103 for the electro stimulation, a frequency input column 104, a duration input column 105 for the electro stimulation, an interval input column 106 for the electro stimulation, and an OK button 107 to decide an input value.

A user inputs a time period between the time of the ON signal from the switch 3 and the time of the start and the end of the electro stimulation in the start time input column 101 and the end time input column 102, respectively. If it is desired to start the electro stimulation right after the operation of the ON switch (not illustrated) in the switch 3, the start time input column 101 should be input as 0 min and 0 sec.

An interval time between the end of the previous electro stimulation and the start of the following electro stimulation is input in the interval input column 106 of the electro stimulation.

The interval time entered in the interval input column 106 is determined by considering the time length from the end of the previous stimulation to the time point when remaining effects carried over from the previous electro stimulation vanishes. For example, if the electro stimulation is applied for 5 min and the effects continue for 6 min measuring from the beginning of the electro stimulation, the appropriate interval time to be set is at least 1 min (the time period during which carried-over effects remain) or more.

Further, default values set for the patients or the previous input values may be displayed by default in the input columns 101-106.

Next, it is determined if the OK button 107 is clicked. If the OK button 107 is clicked, the electro stimulation program containing input contents of the input columns 101-106 as the electro stimulation profile is sent to the generator 10 to complete the processing of the stimulation setting program.

The electro stimulation program is received by the communication unit 14 in the generator 10, and then stored in the memory section (not illustrated) by the control unit 15.

If the patient wearing the switch 3 on his wrist performs an ON command using the ON/OFF switch (not illustrated) of the switch 3 before or during sexual intercourse at a timing designated by the doctor, this ON command is sent by wireless communication to the communication unit 14.

Figure 2:
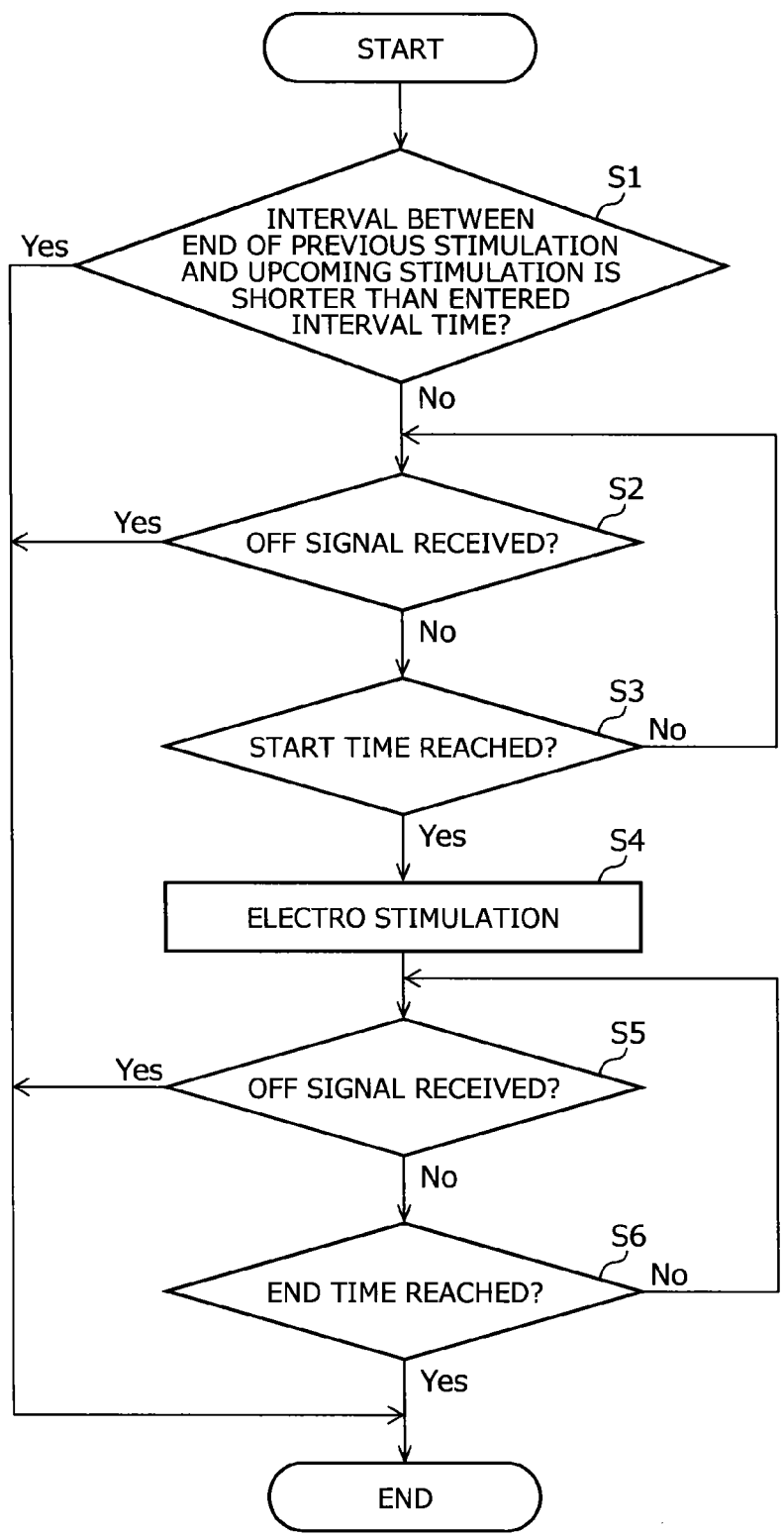
FIG. 2 is a flow chart showing control of an electro stimulation program of an exemplary premature ejaculation treatment device according to the present invention.

After the ON command from the switch 3 is received by the communication unit 14 in the generator 10, a first timer (not illustrated) built in the generator 10 is reset by the control unit 15 to start an electro stimulation processing as shown in the flow chart in FIG. 2. This processing is controlled by the control unit 15 in the generator 10.

In a step S1, it is first determined if the interval time between the end of the previous electro stimulation and the start of the upcoming electro stimulation is shorter than the duration entered in the interval input column 106.

In this step, the amount of time entered in the start time input column 101 is added to the time when the ON command was received from the switch 3 to obtain the scheduled start time of the upcoming electro stimulation, then this scheduled start time is subtracted by the end time of the previous electro stimulation to obtain the interval time between the two electro stimulation. Finally, it is determined whether this interval time is shorter than the time entered in the interval input column 106.

If the interval time between the end of the previous electro stimulation and the start of the scheduled upcoming electro stimulation is shorter than the time entered in the interval input column 106 (step S1: Yes), then the processing is ended.

If the interval time between the end of the previous electro stimulation and the start of the scheduled upcoming electro stimulation is equal to or longer than the time entered in the interval input column 106 (step S1: No), then it is determined whether an OFF signal is received from the switch 3 in a step S2. If the OFF signal is received from the switch 3 (step S2: Yes), then the processing is ended based on the determination that the continuation of the electro stimulation is canceled by the patient.

If the OFF signal is not received from the switch 3 (step S2: No), then it is determined in a step S3 whether the electro stimulation start time is reached by judging if the time entered in the start time input column 101 is satisfied. In this step, it is determined whether the current time reaches the total time calculated by adding the amount of time entered in the start time input column 101 to the time when the ON signal was received from the switch 3.

If the electro stimulation start time is not reached (step S3: No), then the step S2 is repeated to determine if the OFF signal is received from the switch 3.

If the electro stimulation start time is reached (step S3: Yes), in a step S4, the electro stimulation profile stored in the memory section (not illustrated) is read out and output to the stimulation parameter setting unit 16. Subsequently, the stimulation parameter setting unit 16 generates a stimulation intensity modifying signal from the electro stimulation profile and outputs it to the oscillation unit 17, and the oscillation unit 17, in turn, generates an electro stimulation signal from the stimulation intensity modifying signal and outputs it to the pad-type electrode 20. After receiving the electro stimulation signal, the pad-type electrode 20 oscillates an electric signal corresponding to the electro stimulation signal and electrically stimulates the DPNs.

It is determined if the OFF signal is received from the switch 3 in a step S5. If the OFF signal is received from the switch 3 (step S5: Yes), then the processing is ended based on the determination that the continuation of the electro stimulation is canceled by the patient.

If the OFF signal is not received from the switch 3 (step S5: No), then it is determined in the step S6 whether the electro stimulation end time is reached by judging if the time measured in the first timer (not illustrated) reaches the time entered in the end time input column 102.

If the end time is not reached (step S6: No), then the step S5 is repeated to determine if the OFF signal is received from the switch 3.

If the end time is reached (step S6: Yes), then the processing in the flow chart is completed.

Although, in exemplary embodiments of the electro stimulation described above, start and end time of the electro stimulation device 1 are set up by the electro stimulation setting screen 100 in FIG. 3, the present invention is not limited to such embodiment. For example, a pressure sensor and an electrode and the like for detecting erection and bursting of the BSM and the like may be implanted into the penis P or the BSM, and detection signals from these sensors may be used as a trigger to control the timing of the start and end of the electro stimulation. Further, a time period between the detection of the signals and the start and end of the electro stimulation may be set up by the programming wand 2.

Although, in the embodiments described above, the electro stimulation device 1 is controlled by the programming wand 2 operated by the doctor and by the switch 3 operated by the patient, the present invention is not limited to such embodiments, and the programming wand 2 and the switch 3 may be combined to constitute an unified control device having both functions. Further, although, in embodiments, the electro stimulation profile is set up by the doctor, this may be set up by the patient himself or other third parties.

In embodiments, in the processing in FIG. 2, the step S1 may be programmed in such a way that when the interval time between the end of the previous electro stimulation and the start of the scheduled upcoming electro stimulation is equal to or longer than the time entered in the interval input column 106 (step S1: No), it is further determined whether an accumulated value of the electro stimulation period per day exceeds a predetermined time, for example, 60 min. If the accumulated value exceeds the predetermined time, then the processing is ended.

Other features of the invention will become apparent in the course of the following descriptions of exemplary embodiments which are given for illustration of the invention and are not intended to be limiting thereof.

EXAMPLES

Test Example of Method for Treating Premature Ejaculation Using UGR Model

A test was performed to confirm the effectiveness of an exemplary method for treating premature ejaculation according to the present invention using a UGR model in rats.

The employed evaluation system mimics the emission phase in such a way that urethral pressure is raised by infusing saline into the urethra while clamping the glans part of the penis with a clamp, and also realizes the expulsion phase in such a way that multiple rhythmic contractions of BSM are induced to expel the saline from the penis by the rise in urethral pressure and stimulation of the glans part of the penis with the clamp. Furthermore, the multiple rhythmic contractions of BSM observed in the present system are similar to rhythmic contractions of BSM observed during ejaculation in conscious rats and humans. Taken together, this system has been recognized as a system for an ejaculation evaluation (The American Journal of Physiology—Regulatory, Integrative and Comparative Physiology, 303: R737-R747, 2012).

Operations

Figure 4:
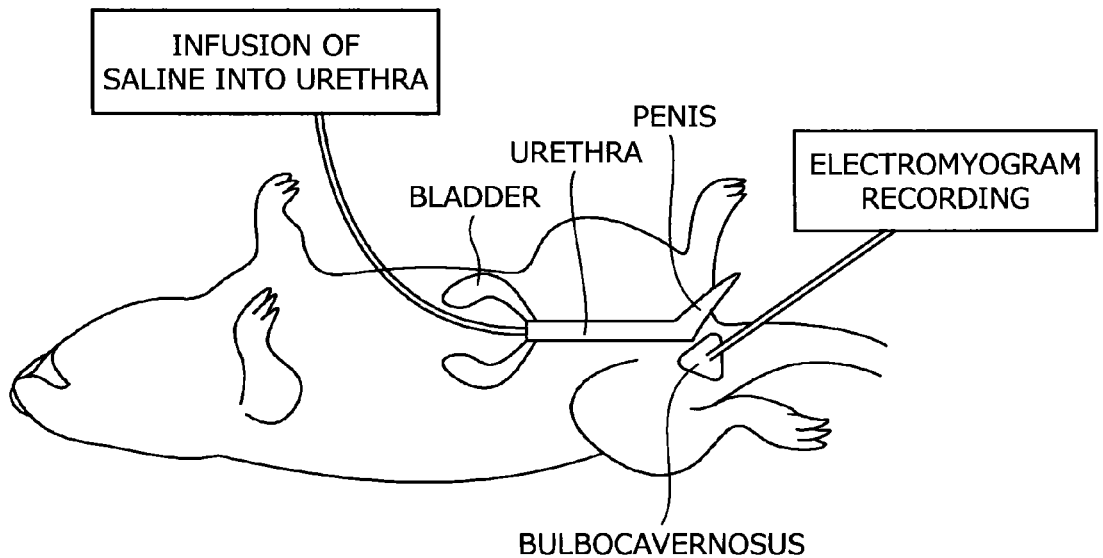
FIG. 4 is a schematic view of an operation in a test example using a urethrogenital reflex (UGR) model to confirm the effectiveness of an exemplary method for treating premature ejaculation according to the present invention.

Male Wistar rats (250-300 g; Japan SLC Inc.) were used. A schematic view of the following operation is shown in FIG. 4.

Rats were anesthetized with 3.0% isoflurane (Mylan Seiyaku) and then subcutaneously injected with 1.2 g/kg urethane (Sigma). After confirming that the rats were sufficiently in an anesthetic state, the spinal cord of each rat was transected at the T8-T10 level. The spinal cord transection was performed at least 90 minutes before the experiment started.

The abdomen was opened to expose the bladder. After the bladder was incised in the upper part, a catheter made of saline-filled polyethylene (PE) tubing (PE-50; Becton Dickinson) was inserted from the incision part through the area just passing the bladder neck. The catheter was tied and fixed in place at the bladder neck. The other end of the catheter was connected to a T-tube to allow continuous saline perfusion (5 μL/s) by an infusion pump (TE-331S; Terumo). The remaining port of the T-tube was connected to a pressure transducer (DX-100; Nihon Kohden) to monitor UPP. In order to allow exposure of the glans from the foreskin, a suture was passed through the tip of the penis in a loose loop, so that the glans was exposed from the foreskin by pulling the suture.

After a perineal skin incision was made to expose the BSM, stainless-steel electrodes were placed thereon for recording BSM-electromyogram (BSM-EMG). After DPNs were exposed by exfoliation on both sides of the penis, a cuff electrode (Unique Medical Co. Ltd.) connected to an electro stimulation device was wound around the DPNs on both sides of the penis for application of an electro stimulation. UPP and BSM-EMG activity data were acquired using LabChart (version 7, ADInstruments) for analysis.

Experiments

The glans was exposed from the foreskin by 1-1.5 cm by pulling the ligature through the glans, and the glans part was clamped by a clamp (120 g/mm$^2$). The clamp was removed when a BSM-burst characterized by typical large amplitude and high frequency was observed. The number of BSM-bursts occurring after removal of the clamp was measured. The electro stimulation was applied under the condition of 0.1 mA, 100-3,000 Hz, and 100 μsec immediately before putting the clamp on the penis until after removing the clamp. Preset values were measured in the same animal before the electro stimulation experiments. The electro stimulation was initiated with a stimulation frequency of 100 Hz and increased, in a frequency-dependent manner, to 300, 1,000, and 3,000 Hz at 10 min intervals. The UGR was performed again without applying the electro stimulation after the experiment with 3,000 Hz to confirm that the reaction of BSM-burst was recovered within 30 min.

That is, in the performed experiments, the UGR was first performed without applying the electro stimulation to obtain the preset values (preset value acquisition session), then the UGR was performed with the electro stimulation (electro stimulation session), where the electro stimulation with the frequency of 100, 300, 1,000, and 3,000 Hz was applied at 10 min intervals in a frequency-dependent manner, and finally the UGR was again performed without applying the electro stimulation (recovery confirmation session) to complete one set of experiments using the same animal. Six animals were used for this experiments (n=6).

Results

Figure 7:
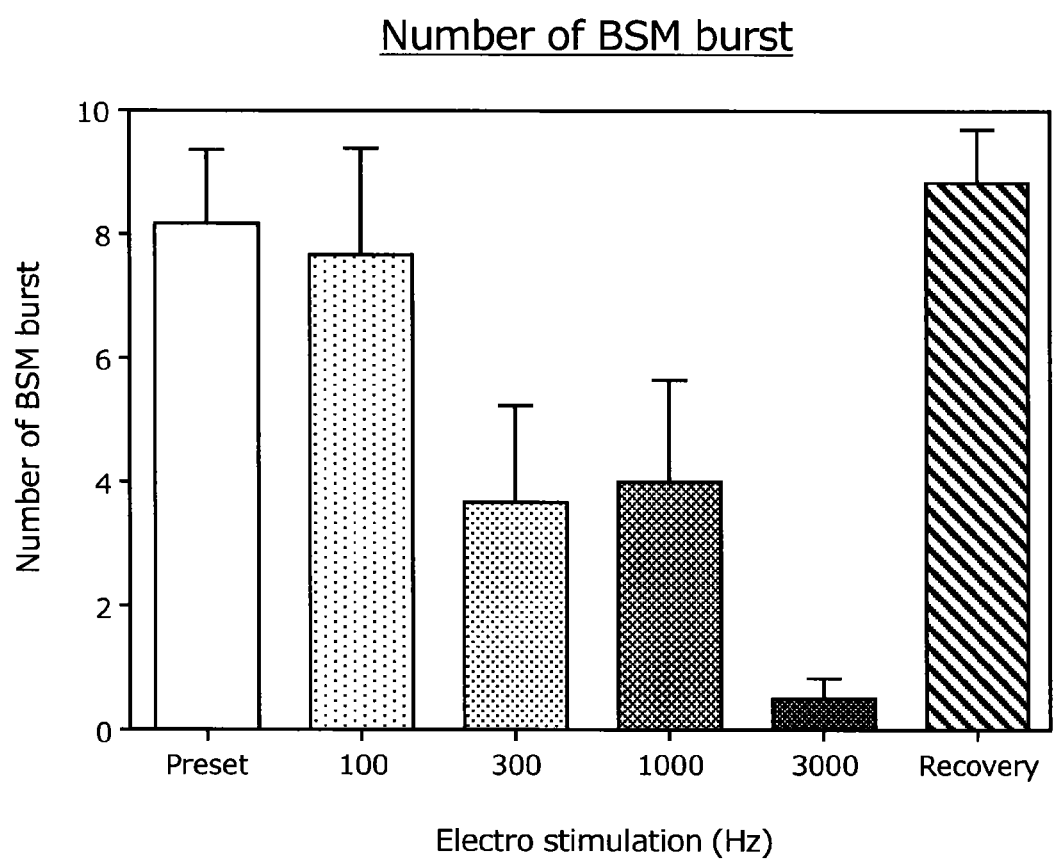
FIG. 7 is a graph showing measurement results of the number of BSM bursts using the UGR model obtained in the preset value acquisition session without the electro stimulation, in the electro stimulation session with parameter values of 0.1 mA, 100 μsec, and 100, 300, 1,000, and 3,000 Hz, and in a recovery session without the electro stimulation.

The results of the performed experiments are shown in FIGS. 5-7.

FIG. 5(a) shows changes in UPP and FIG. 5(b) shows changes in BSM-EMG in the preset value acquisition session. The start time of clamping is indicated by "clamp" on the left side of FIG. 5(a).

The UPP increased by clamping the penis, and then the BSM-burst having a high frequency and large amplitude was observed in BSM-EMG at the arbitrary time after the clamping. The clamp was removed at this time point (time points indicated by a dotted vertical line in FIGS. 5(a) and (b)).

In the course of the experiments shown in FIG. 5, after the removal of the clamp, many BSM-bursts were induced with the saline expulsion from the penis in an ejaculatory-like manner.

FIG. 6(a) shows changes in UPP and FIG. 6(b) shows changes in BSM-EMG in the electro stimulation session with 0.1 mA, 3,000 Hz, and 100 μsec using an arbitrary rat.

As shown in FIG. 6(b), the BSM-burst after the removal of the clamp was completely suppressed by the electro stimulation (indicated by a dotted ellipse in FIG. 6(b)).

FIG. 7 shows a graph depicting the number of BSM-bursts in the preset value acquisition session without the electro stimulation, in the electro stimulation session with 100, 300, 1,000, and 3,000 Hz, and in the recovery confirmation session without the electro stimulation. The number of BSM bursts was reduced with the frequency of 300, 1,000, and 3,000 Hz, especially down to about 1/10 in case of 3,000 Hz. This reduction was not observed without applying the electro stimulation (in the recovery confirmation session).

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of treating premature ejaculation, comprising:
   arranging one or more electrodes to face dorsal penile nerves (DPNs) of a patient with premature ejaculation; and
   applying an electro stimulation having a frequency and a current by which seminal fluid expulsion is not immediately induced in the patient by the one or more electrodes during a time period from before the start of sexual intercourse to ejaculation;
   wherein:
   applying the electro stimulation comprises applying the electro stimulation for a period of time that does not exceed 60 minutes per day; and
   the electro stimulation reversibly extends an intravaginal ejaculatory latency time (IELT) of the patient.

2. The method according to claim 1, wherein the frequency of the electro stimulation is 100-5,000 Hz.

3. The method according to claim 1, wherein arranging one or more electrodes comprises implanting one or more electrodes surgically under skin at a proximal portion of the penis of the patient in contact with DPNs.

4. The method according to claim 1, wherein arranging one or more electrodes comprises arranging one or more electrodes to face less than all DPNs of the patient.

* * * * *